United States Patent [19]

Heiland

[11] Patent Number: 4,817,820

[45] Date of Patent: Apr. 4, 1989

[54] SLIDE DISPENSER FOR A REAGENT CANNISTER

[75] Inventor: Robert Heiland, Goshen, Ind.

[73] Assignee: Miles Inc., Elkhart, Ind.

[21] Appl. No.: 90,234

[22] Filed: Aug. 27, 1987

[51] Int. Cl.⁴ .............................................. B65G 59/02
[52] U.S. Cl. ..................................... 221/279; 312/71; 206/817
[58] Field of Search ................. 221/58, 198, 232, 279, 221/280; 312/61, 71; 453/48, 51, 52, 53, 54; 206/817; 220/93; 222/386.5

[56] References Cited

U.S. PATENT DOCUMENTS

| | | | |
|---|---|---|---|
| 2,656,233 | 10/1953 | Bollmann | 221/57 X |
| 3,140,132 | 7/1964 | Jackson | 312/71 X |
| 3,393,831 | 7/1968 | Stewart | 221/232 |
| 3,393,948 | 7/1968 | Brefka | 312/61 |
| 3,589,557 | 6/1971 | Johnson | 221/279 X |
| 3,604,562 | 9/1971 | Loeffler | 221/279 X |
| 4,187,077 | 2/1980 | Covington et al. | 221/279 X |

Primary Examiner—F. J. Bartuska
Attorney, Agent, or Firm—Roger N. Coe

[57] ABSTRACT

A two-piece slide dispenser includes a housing defining an internal compartment for the storage of a plurality of reagent slides or similar items. The housing includes a dispensing opening and a loading opening. A finger or similar structure at least partially obstructs the dispensing opening to prevent inadvertant falling out of the reagent slides. A one-piece, multiple function, resilient spring boot including a biasing portion and a light and humidity sealing portion is also provided. Once reagent slides are loaded through the loading opening into the internal compartment, the spring boot is mounted in the compartment to engage the slides biasing them toward the dispensing opening. The biasing portion of the spring boot can be hemispherical or of a similar configuration allowing this portion to fold into itself. The biasing portion also includes an extension extending from the hemisphere to engage the slides. The sealing portion of the spring boot includes a lip or edge that can be secured on the housing around the loading opening. In an alternative embodiment, the lip or edge of the spring boot engages the inner peripherial surface of the housing adjacent the loading opening and the loading opening is closed by a cap.

17 Claims, 2 Drawing Sheets

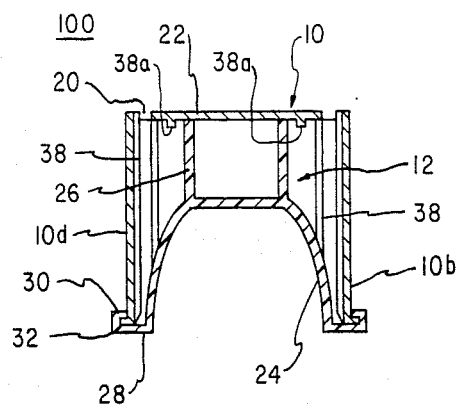
FIG. 2
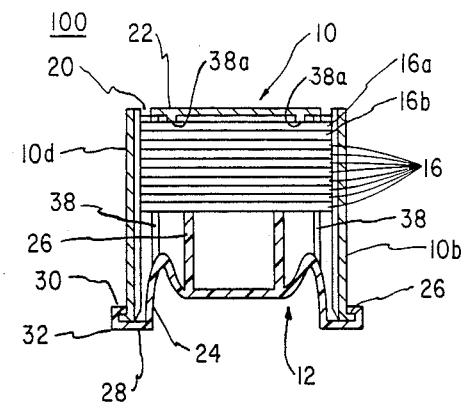
FIG. 3
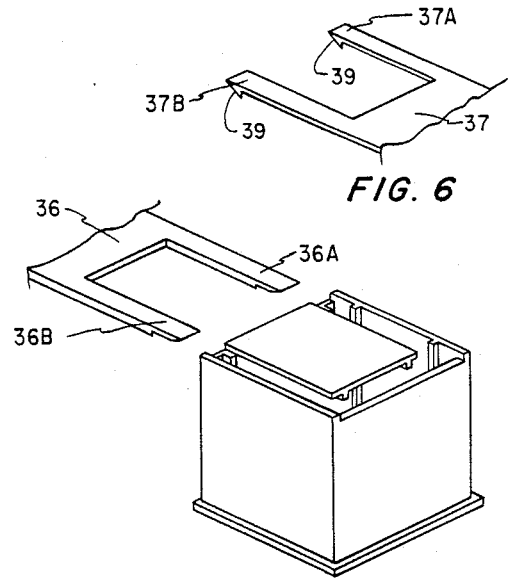
FIG. 6
FIG. 4
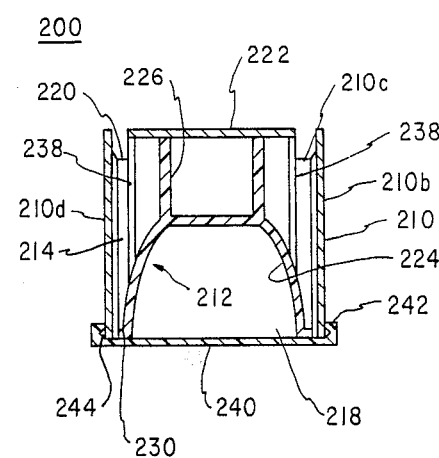
FIG. 5

SLIDE DISPENSER FOR A REAGENT CANNISTER

BACKGROUND OF THE INVENTION

A. Field of the Invention

The present invention relates to a new and improved device for dispensing reagent strips, reagent slides and the like, and more particularly, to a new and improved slide dispenser with a one-piece, multiple function, resilient spring boot that provides both a biasing force for dispensing slides, strips and the like and a light and humidity seal to inhibit deterioration of the strips, slides and the like.

B. Description of the Prior Art

Reagent strips, slides and the like are used to determine different substances in body fluids such as blood. In certain situations high speed, automated instruments use reagent strips, slides or the like. Such instruments require reliable feeding of individual strips, slides and the like to allow high speed operation. In addition to reliability of the dispenser, it is preferred that the dispenser be inexpensive allowing disposal after use of all of the slides, strips and the like in the dispenser. Since reagent strips, slides and the like are sensitive to light and humidity, it is also preferred that the dispenser include a seal or similar structure to block these environmental affects and prevent damage to the strips, slides and the like.

In the past, dispensers of this type have required several components. In addition to a dispenser housing, a spring to bias the strips, slides or the like to the dispenser opening and a cap to seal the interior of the housing were required. Examples of dispensers of this type are disclosed in U.S. Pat. Nos. 2,656,233; 3,393,948; 3,589,557 and 4,187,077. Due to multiple components, the cost of these dispensers is increased. This increased cost eliminates the disposability feature of these dispensers.

In addition to dispensers that use springs, some dispensers use gravity to feed the items to be dispensed. Gravity feed dispensers suffer from a problem of decreased reliability since there is not a positive force biasing the items to be dispensed toward the dispensing opening. This results in misfeeding and jamming of the instrument.

SUMMARY OF THE INVENTION

An object of the present invention is to provide a new and improved dispenser for reagent strips, slides and the like.

Another object of the present invention is to provide a new and improved spring boot for a dispenser of reagent strips, slides and the like.

A further object of the present invention is to provide a new and improved one-piece, multiple function resilient spring boot for a dispenser used for dispensing reagent strips, slides and the like.

A still further object of the present invention is to provide a new and improved one-piece, multiple function spring boot for a dispenser of reagent strips, slides and the like that includes both a biasing portion and a light and humidity sealing portion.

Briefly, the present invention is directed to a new and improved dispenser for reagent strips, slides and the like. The dispenser includes a housing defining an internal compartment for containing a plurality of reagent strips, slides and the like. The housing includes a dispensing opening and a loading opening. A finger or similar structure at least partially obstructs the dispensing opening to prevent accidental dispensing of the items contained in the internal compartment.

A one-piece, multiple function spring boot is mounted in the internal compartment and functions to bias the items to be dispensed toward the dispensing opening. The spring boot includes a biasing portion and a sealing portion. The biasing portion is a hemispherical body or a similar configuration that allows the body to fold into itself Included with the biasing portion is an extension extending from the body. When mounted in the internal compartment, the extension engages the items to be dispensed and transmits the biasing force of the body to these items.

The sealing portion of the spring boot includes a lip or edge that is secured to the housing around the loading opening This mechanical seal inhibits passage of humidity and light into the internal compartment.

In an alternative embodiment, the lip or edge of the sealing portion of the spring boot fits into the internal compartment and seals along the inner periphery of the compartment adjacent the loading opening A cap can then be secured over the loading opening to secure the spring boot and further seal the internal compartment from light and humidity.

BRIEF DESCRIPTION OF THE DRAWINGS

The above and other objects and advantages and novel features of the present invention will become apparent from the following detailed description of a preferred and alternative embodiments of the invention illustrated in the accompanying drawings wherein:

FIG. 2 is a generally vertical, cross-sectional view of the dispenser with the mounted spring boot;

FIG. 3 is a view similar to FIG. 2 with a plurality of reagent slides or strips mounted in the dispenser;

FIG. 4 is a perspective view illustrating the dispensing of slides using a blade;

FIG. 5 is a view similar to FIG. 2 illustrating an alternative embodiment of a dispenser and spring boot with an end cap; and FIG. 6 is a perspective view of a puller used for dispensing slides from the dispenser of the present invention.

DESCRIPTION OF THE PREFERRED EMBODIMENT

Figure 1:
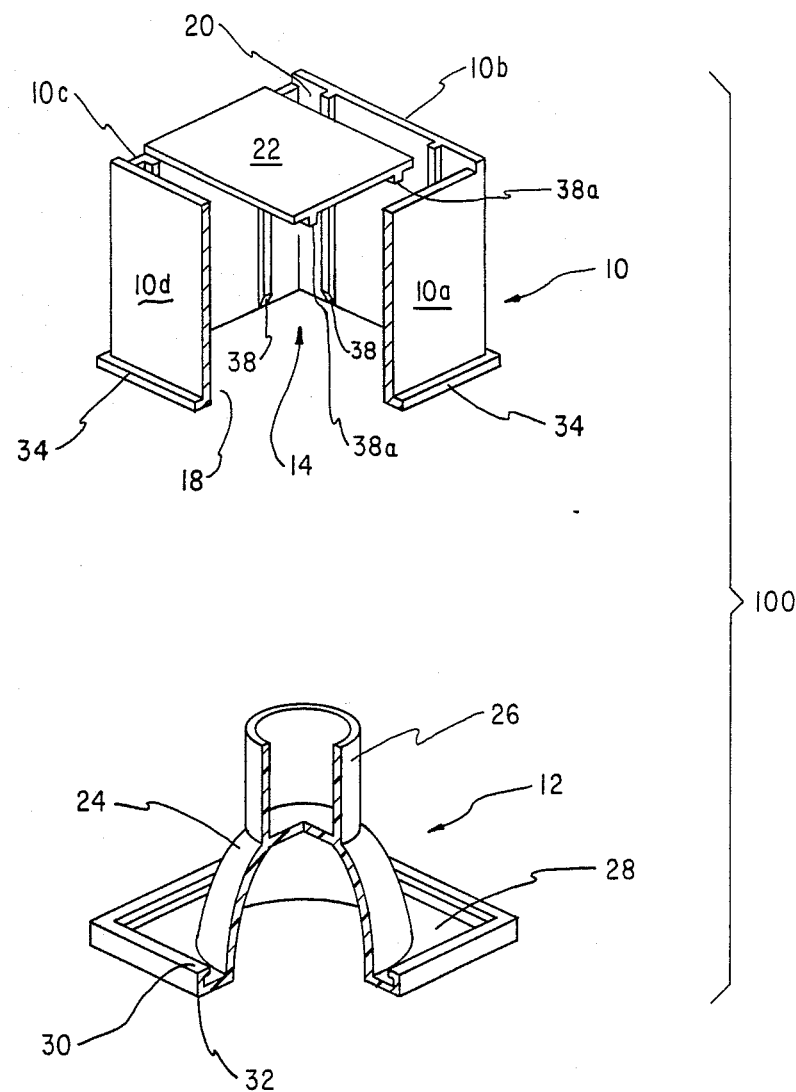
FIG. 1 is a perspective, partially cut-away view of a dispenser housing and a one-piece, multiple function spring boot constructed in accordance with the principles of the present invention.

Referring initially to FIGS. 1-4, a dispenser 100 for dispensing reagent slides or similar items is illustrated. Dispenser 100 can be used in automated instruments and it is desirable that it be of a cost allowing disposal after use. The cost of the dispenser 100 is reduced not only by the material that can be used to manufacture it but also by a minimization of parts. Dispenser 100 requires only two components, a cannister or housing 10 and a one-piece, multiple function spring boot 12. Housing 10 is illustrated as square or rectangular in configuration but it can be of any configuration as required by the items to be dispensed. Housing 10 is made of inexpensive material such as plastic that can be easily molded or assembled thereby minimizing the cost of manufacture and allowing disposal after use.

The number of components in dispenser 100 is minimized since the one-piece spring boot 12 performs three functions. Spring boot 12 functions both as a light seal and as a humidity seal These sealing functions are important since light and humidity can damage or deteriorate reagent slides and strips carried in dispenser 100. The spring boot 12 also applies pressure on the reagent slides to assist dispensing and to prevent the reagent slides from falling out of the cannister 10.

Housing 10, in the preferred embodiment, is square with sides 10a, 10b, 10c and 10d. An internal compartment 14 for the containment of a plurality of reagent slides 16 (FIG. 3) is defined in housing 10. Slides 16 are loaded into compartment 14 through a first, loading opening 18 The slides 16 can also be loaded through a dispensing opening 20. When dispensed, the reagent slides 16 pass through the dispensing opening 20. A finger or obstruction 22 is integrally formed on side 10c and extends at least partially over opening 20 to prevent slides 16 from accidentally falling out of housing 10, and also to provide an obstruction at opening 20 allowing dispensing through the use of an instrument such as a blade. Preferably, finger 22 is not the same width as opening 20.

To allow each slide 16 to be dispensed individually and as rapidly as required by an automated instrument, slides 16 in compartment 14 are biased upwardly against finger 22 by the one-piece, multiple function spring boot 12. To provide a biasing force, spring boot 12 is fabricated of a resilient material such as silicone rubber.

The biasing pressure on slides 16 must be of a magnitude to allow easy and rapid dispensing of the slides 16 but not too large so as to make it difficult to remove the slides 16 individually. It has been discovered that spring boot 12 provides the proper magnitude of consistent pressure during dispensing of all slides 16 ensuring uninterrupted dispensing. The biasing pressure is provided from a hemispherical body portion 24 and an integral tubular extension 26 of spring boot 12. In the preferred embodiment, body portion 24 is illustrated as being of a hemispherical configuration. This configuration provides the spring action of spring boot 12 by allowing the body portion 24 to be compressed or folded into itself while slides 16 (FIG. 3) are in compartment 14. Since body portion 24 folds into itself, less space in housing 10 is required As slides 16 are dispensed, body portion 24 moves toward its original, unloaded configuration (FIG. 2). From the fully compressed position (FIG. 3) to the static, unloaded position, body portion 24 provides a substantially even push or pressure on the slides 16. Since the even biasing pressure during dispensing of all of the slides 16 is the object of spring boot 12, configurations other than hemispherical can also be used.

Tubular extension 26 is a force transmission member, and also functions to take up space when the spring boot 12 is folded into itself. Tubular extension 26 extends between body portion 24 of spring boot 12 and the bottom slide 16 in compartment 14. Extension 26 maintains contact between body portion 24 and slides 16 and transmits the biasing force developed by body portion 24 to the slides 16 through the complete range of movement of body portion 24 (FIG. 3 to FIG. 2).

The one-piece, multiple function spring boot 12 also functions to seal compartment 14 and slides 16 from light and humidity Spring boot 12 includes a base 28 with a reverse lip 30 along a bottom edge 32. The base 28 is substantially the same configuration as compartment 14 providing a secure fit of spring boot 12 in compartment 14 and opening 18. The base 28 and lip 30 allows spring boot 12 to seal compartment 14 from light and humidity particularly while dispenser 100 is in an automated instrument. Base 28 completely covers loading opening 18 and lip 30 snaps over a flange or detent 34 formed at the lower end of sides 10a, 10b, 10c and 10d surrounding opening 18. Once lip 30 is secured over flange 34, base 28 and lip 30 is secured over flange 34, base 28 and lip 30 function to seal opening 18 from light and humidity thereby protecting slides 16 from the harmful affects of these elements In the past, a separate cap was required to cover end 18. The need for this third part (the separate cap) is eliminated by the one-piece, multiple function spring boot 12 of the present invention.

In preparation for use of dispenser 100, a plurality of slides 16 are loaded into internal compartment 14 through loading opening 18 or dispensing opening 20 A one-piece, multiple function spring boot 12 is then placed into compartment 14 and reverse lip 30 is snapped over flange 34 (FIG. 3). Slides 16 are now biased into engagement with finger 22 and are ready to be dispensed.

One method of dispensing slides 16 is illustrated in FIG. 4. In accordance with this method, a blade 36 with a forked configuration is moved with tangs 36A and 36B passing along the sides of finger 22 into engagement with the top slide 16a. The lower surface of finger 22 could include two ribs 38a functioning as spacers to space slide 16 slightly from finger 22. This spacing allows slide 16 to slide without scratching its surface. By extending blade 36, slide 16a is pushed out of dispenser 100 to a desired location in a measuring instrument. Blade 36 is then retracted and the next slide 16b moves under biasing pressure from spring boot 12 into engagement with finger 22 ready to be dispensed by blade 36. Blade 36 functions as a pusher but a puller 37 could be used. The puller 37 would pass over the top slide 16 in a direction opposite to the direction of movement of pusher 36. Edges 39 on tangs 37A and 37B of puller 37 engage top slide 16 and pull it out of dispenser 100 as the puller 37 is pulled or retracted from opening 20.

To improve dispensing of slides 16, additional ribs 38 can be formed on the inner peripheral surfaces of walls 10a, 10b, 10c and 10d. These ribs 38 engage the peripheral edges of slides 16 minimizing the surface area of engagement between walls 10a, 10b, 10c and 10d and slides 16. This smaller surface area reduces the frictional force acting in opposition to the biasing pressure of the one-piece, multiple function spring boot 12 improving the dispensing reliability of dispenser 100.

An alternative embodiment of dispenser 100 is illustrated in FIG. 5 and designated by reference numeral 200. Dispenser 200 is similar to dispenser 100 in that it includes a housing 210 defining an internal compartment 214. Compartment 214 serves for the containment of slides 16. Housing 210 includes walls 210a, 210b, 210c and 210d with ribs 238 on the inner peripheral surfaces. Housing 210 further includes a loading opening 218 for loading slides 16 into compartment 214 and a dispensing and/or loading opening 220. The dispensing opening 220 is partially obstructed by a finger 222 against which slides 16 are biased by a spring boot 212.

Spring boot 212 is similar to spring boot 12 in that it includes a hemispherical body portion 224 and a tubular extension 226. Both the body portion 224 and the tubular extension 226 function the same as the corresponding components of spring boot 12 Spring boot 212 differs, however, from spring boot 12 in the sealing portion Instead of a reverse lip, spring boot 212 includes a lower sealing lip or edge 230 that seals against the inner peripheral surfaces of walls 210a (not shown), 210b, 210c and 210d once spring boot 212 is positioned in compartment 214. This seal inhibits the passage of light and humidity into compartment 214 minimizing the deteriorating effects on slides 16 To provide the best seal, the bottom of body portion 224 and lip 230 are substantially the same configuration as compartment 214.

An additional seal and cover to close loading opening 218 is provided by a cap 240 that can be secured over loading opening 218. Cap 240 is preferably fabricated of the same material as housing 210 and can be snap fit onto housing 210. A snap fit is provided by a reverse lip 242 on cap 240 that snaps over a detent 244 formed on the outer peripheral surface of each wall 210a (not shown), 210b, 210c and 210d adjacent loading opening 218. Once secured on detent 244, cap 240 provides an additional seal against light and humidity and provides a rigid closure over loading opening 218 Cap 240 also secures spring boot 212 in compartment 214. Since the material of cap 240 is inexpensive, alternate dispenser 200 is disposable after use.

Dispenser 200 can be used with an automatic instrument in the same manner as dispenser 100. Blade 36 engages and dispenses individual slides 16 and spring boot 212 applies constant and uniform pressure to the slides 16 to ensure reliable dispensing.

Many modifications and variations of the present invention are possible in light of the above teachings. Thus, it is to be understood that, within the scope of the appended claims, the invention can be practiced other than as specifically described in the above description.

What is claimed and sought to be secured by United States Letters Patent is:

1. A slide dispenser for a cannister, comprising:
    a housing, said housing defining a compartment for the containment of a plurality of slides,
    a slide dispensing opening in said housing, and
    a one piece, hemispherically shaped, collapsible, spring boot in said compartment for biasing said slides toward said slide dispensing opening, said spring boot including a slide biasing portion, a slide engaging extension extending from said slide biasing portion and a light and humidity sealing portion.

2. A slide dispenser for a cannister as set forth in claim 1 further comprising means for preventing said slides from inadvertently falling out of said slide dispensing opening.

3. A slide dispenser for a cannister as set forth in claim 1 wherein said housing includes a slide loading opening, said spring boot includes means for securing at least a portion of said spring boot over said slide loading opening.

4. A slide dispenser for a cannister as set forth in claim 1 wherein said housing includes a slide loading opening, cap means for securement over said slide loading opening for retaining said spring boot and closing said slide loading opening.

5. A slide dispenser for a cannister as set forth in claim 1 wherein said light and humidity sealing portion of said spring boot includes an end section sealingly fitted within said compartment.

6. A slide dispenser for a cannister as set forth in claim 1 further comprising a slide loading opening in said housing, said light and humidity sealing portion including lip means for fitting over said housing around said slide loading opening.

7. A slide dispenser for a cannister as set forth in claim 1 wherein said spring boot is of elastomeric material.

8. A slide dispenser for a cannister as set forth in claim 1 wherein said spring boot is of silicone rubber.

9. An apparatus for dispensing reagent slides or the like, comprising:
    a housing,
    a compartment within said housing for holding a plurality of reagent slides or the like,
    a first opening in said housing for distribution or loading of said reagent slides or the like, and
    a one-piece, collapsible spring member positioned in said compartment including a first portion with a hemispherical body and a tubular extension extending from said body engaging and biasing said reagent slides or the like toward said first opening and a second portion sealing said second opening.

10. An apparatus for dispensing reagent slides or the like as claimed in claim 9 wherein said one-piece spring member is elastomeric.

11. An apparatus for dispensing reagent slides or the like as claimed in claim 9 wherein said one-piece spring member is elastomeric with a lip portion engaging said housing and sealing said second opening.

12. An apparatus for dispensing reagent slides or the like as claimed in claim 9 further comprising a second opening in said housing for loading said reagent slides or the like into said compartment.

13. An apparatus for dispensing reagent slides or the like as claimed in claim 12 further comprising a cap secured to second opening.

14. A one-piece biasing and sealing spring member for a reagent slide dispenser, comprising:
    a hollow, unitary resilient body, said body including a chamber portion of a hemispherically shaped configuration allowing said body to fold into said chamber portion, a slide engagement portion extending from said chamber portion, and lip portion means for mechanically sealing said dispenser from light and humidity.

15. A one-piece biasing and sealing spring member for a reagent slide dispenser as set forth in claim 14 wherein said hollow, unitary resilient body is of elastomeric material.

16. A one-piece biasing and sealing spring member for a reagent slide dispenser as set forth in claim 14 wherein said hollow, unitary resilient body is of a silicone rubber.

17. A one-piece biasing and sealing spring member for a reagent slide dispenser as claimed in claim 14 wherein said slide engagement portion is a tubular extension.

* * * * *